(12) United States Patent
Palti et al.

(10) Patent No.: US 12,023,168 B2
(45) Date of Patent: Jul. 2, 2024

(54) ELECTROPHYSIOLOGICAL (EP) MAP COLORATION BY CONSIDERING OUTLIERS

(71) Applicant: BIOSENSE WEBSTER (ISRAEL) LTD., Yokneam (IL)

(72) Inventors: Yair Palti, Herzelia (IL); Israel Zilberman, Yokneam (IL); Assaf Govari, Haifa (IL); Vadim Gliner, Haifa (IL); Andres Claudio Altmann, Zichron Ya'acov (IL); Gili Attias, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 17/235,986

(22) Filed: Apr. 21, 2021

(65) Prior Publication Data

US 2022/0338783 A1 Oct. 27, 2022

(51) Int. Cl.
*A61B 5/327* (2021.01)
*A61B 5/287* (2021.01)
*A61B 5/343* (2021.01)
*A61B 5/367* (2021.01)

(52) U.S. Cl.
CPC .............. *A61B 5/367* (2021.01); *A61B 5/287* (2021.01); *A61B 5/327* (2021.01); *A61B 5/343* (2021.01)

(58) Field of Classification Search
CPC ................................ A61B 5/367; A61B 5/327
USPC ....................................................... 600/523
See application file for complete search history.

(56) References Cited

U.S. PATENT DOCUMENTS

| 7,809,421 B1 * | 10/2010 | Govari | ................... G01V 13/00 600/407 |
| 8,456,182 B2 | 6/2013 | Bar-Tal et al. | |
| 9,186,081 B2 | 11/2015 | Afonso et al. | |

(Continued)

FOREIGN PATENT DOCUMENTS

| EP | 973876 A1 | 1/2000 | |
| WO | WO-2019238804 A1 * | 12/2019 | ............... G06K 9/34 |

OTHER PUBLICATIONS

European Search Report for corresponding EPA No. 22168991.2 dated Sep. 15, 2022.

(Continued)

*Primary Examiner* — Nicole F Lavert
(74) *Attorney, Agent, or Firm* — Dergosits & Noah LLP; Todd A. Noah

(57) ABSTRACT

A method includes receiving a plurality of data points including electrophysiological (EP) values measured at respective positions in at least a portion of an organ of a patient. Some of the EP values are classified as outlier values in accordance with a defined criterion. A visual representation of at least the portion of the organ is derived from the plurality of data points. The visual representation represents the EP values with respective colors, and visualizes less than all the outlier values, by performing one or both of (a) identifying outlier values that deviate from respective neighboring EP values by less than a defined deviation, and representing the outlier values using colors that match the neighboring EP values, and (b) setting for the visual representation a mapping, which maps the EP values to the colors and which excludes at least some of the outlier values.

12 Claims, 4 Drawing Sheets

(56) References Cited

U.S. PATENT DOCUMENTS

| | | | | |
|---|---|---|---|---|
| 2007/0106146 | A1* | 5/2007 | Altmann | A61B 6/5247 600/407 |
| 2013/0274582 | A1* | 10/2013 | Afonso | A61B 5/065 600/374 |
| 2019/0192029 | A1* | 6/2019 | Curtin | A61B 5/366 |
| 2019/0340753 | A1* | 11/2019 | Brestel | G16H 15/00 |
| 2021/0177294 | A1* | 6/2021 | Gliner | A61B 1/00045 |

OTHER PUBLICATIONS

Biosense Webster Inc.: "CARTO 3 System—Instructions for Use = UG-5400-006h (O5A)", Mar. 10, 2019, pp. 1-291 XP055838225.

\* cited by examiner

ELECTROPHYSIOLOGICAL (EP) MAP COLORATION BY CONSIDERING OUTLIERS

FIELD OF THE INVENTION

The present invention relates generally to electrophysiological mapping, and particularly to visualization of cardiac electrophysiological maps.

BACKGROUND OF THE INVENTION

Electrophysiological (EP) cardiac mapping may use visualizations methods previously proposed in the patent literature, to ease an interpretation of an EP map. For example, U.S. Pat. No. 9,186,081 describes an efficient system for diagnosing arrhythmias and directing catheter therapies that may allow for measuring, classifying, analyzing, and mapping spatial electrophysiological (EP) patterns within a body. The efficient system may use an electronic control system (ECU) for computing and providing the user with a variety of metrics, derivative metrics, high definition (HD) maps, HD composite maps, and general visual aids for association with a geometrical anatomical model shown on a display device. In one embodiment, out-of-range colors that may be chosen to indicate values that are out of a range of interest. In another embodiment, a function may use the minimum value and the maximum value in an image as the default limits of the "color axes", with all the colors of the colormap being used to represent values between these limits. If the minimum or maximum value is an outlier, the image will be displayed with lower contrast because most of the colors from the colormap will be underutilized, while a few colors will be used to represent the majority of the data. The solution to this problem is to discard or ignore the outliers.

SUMMARY OF THE INVENTION

An embodiment of the present invention that is described hereinafter provides a method including receiving a plurality of data points including electrophysiological (EP) values measured at respective positions in at least a portion of an organ of a patient. Some of the EP values are classified as outlier values in accordance with a defined criterion. A visual representation of at least the portion of the organ is derived from the plurality of data points. The visual representation (i) represents the EP values with respective colors and (ii) visualizes less than all the outlier values, by performing one or both of (i) identifying outlier values that deviate from respective neighboring EP values by less than a defined deviation, and representing the outlier values using colors that match the neighboring EP values, and (ii) setting for the visual representation a mapping, which maps the EP values to the colors and which excludes at least some of the outlier values. The visual representation is displayed to a user.

In some embodiments, receiving the data points includes acquiring the data points using a catheter.

In some embodiments, deriving the visual representation includes deriving an anatomical map. In other embodiments, deriving the anatomical map includes generating the anatomical map by fast anatomical mapping (FAM).

In an embodiment, the EP values are one of local activation times (LATs), bipolar potentials, and unipolar potentials.

In another embodiment, deriving the visual representation includes interpolating over the EP values not classified as outlier values.

In yet another embodiment, wherein representing the outlier values using colors that match the neighboring EP values includes coloring the outlier values according to a color code used in interpolating the EP values.

There is additionally provided, in accordance with another embodiment of the present invention, a system including an interface and a processor. The interface is configured to receive a plurality of data points including electrophysiological (EP) values measured at respective positions in at least a portion of an organ of a patient. The processor is configured to (a) classify some of the EP values as outlier values in accordance with a defined criterion, (b) derive, from the plurality of data points, a visual representation of at least the portion of the organ that (i) represents the EP values with respective colors and (ii) visualizes less than all the outlier values, by performing one or both of: identifying outlier values that deviate from respective neighboring EP values by less than a defined deviation, and representing the outlier values using colors that match the neighboring EP values, and setting for the visual representation a mapping, which maps the EP values to the colors and which excludes at least some of the outlier values, and (c) display the visual representation to a user.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
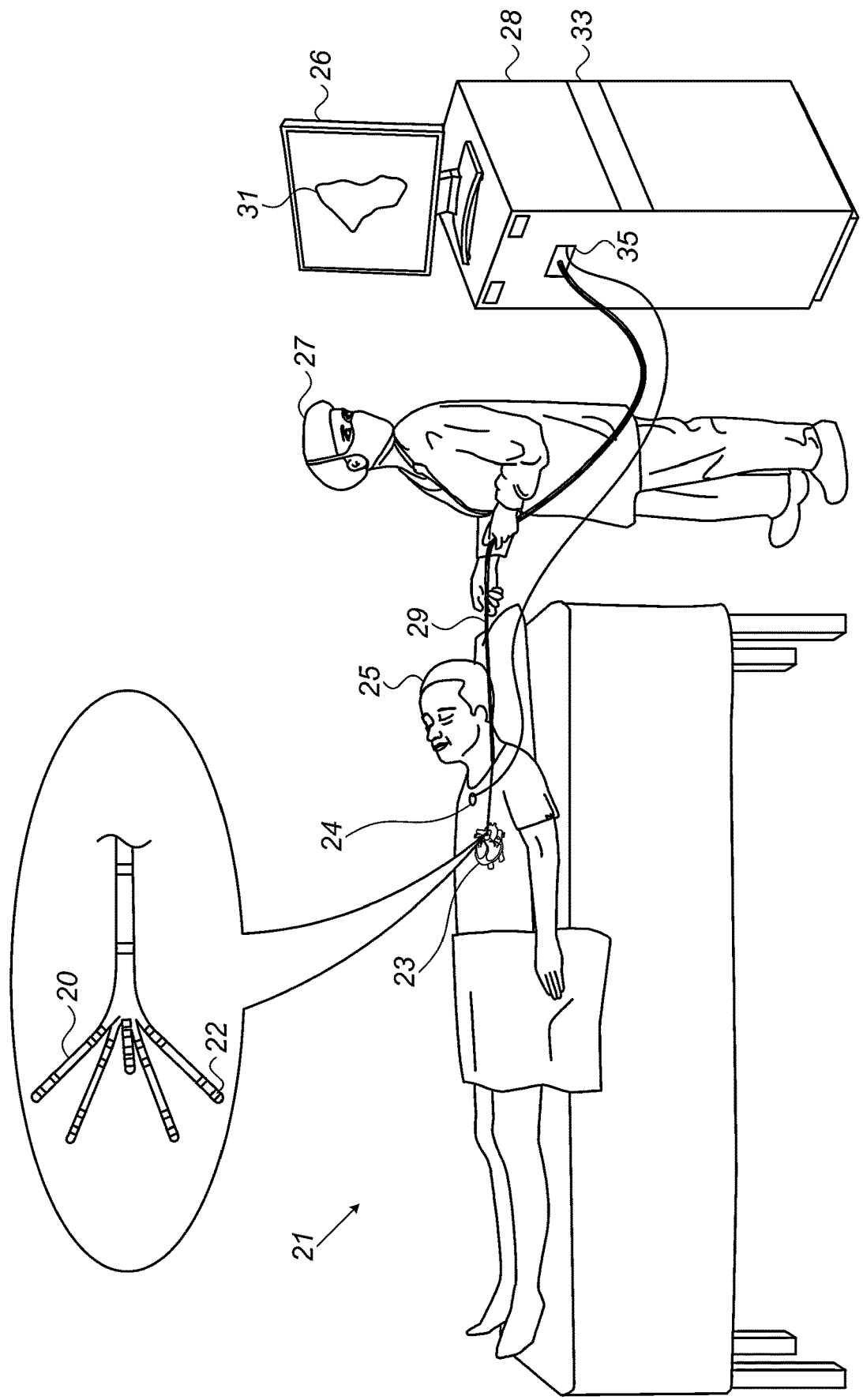
FIG. 1 is a schematic, pictorial illustration of a system for electrophysiological (EP) mapping, in accordance with an exemplary embodiment of the present invention.

Catheter-based electrophysiological (EP) mapping techniques may produce various types of EP maps of an organ, such as an atrium of a heart. Cardiac EP maps, such as a local activation time (LAT) map, a bipolar potential map, or a unipolar potential map, may be produced by acquiring electrograms from multiple locations on a heart chamber surface. EP values, such as LATs (or potentials), can then be derived from the electrograms for the respective locations. Such an EP map can be obtained by interpolating over EP values, with outlier EP values excluded from interpolation. The HP map can then be overlayed, e.g., using a color scale, onto a 3D anatomical map of the chamber.

The locations and respective EP values, called hereafter "data points," can also be subsequently overlaid onto the 3D map. In particular, the acquired EP values (e.g., LAT or peak-to-peak voltage values), including outlier data points, are typically displayed as a colored map using a color palette that assigns a range of colors for a range of the EP values. However, if the range of EP values is large, for example due to the presence of the outlier EP values, small differences of attribute values will be difficult or impossible to see as color differences.

In the context of the present disclosure, the term "outlier data points" refers to acquired EP values that are different from their nearest neighbors by at least a predetermined value, for example EP values distorted due to positions that are too deep inside the cavity, or too far out of tissue surface.

Some embodiments of the present invention that are described hereinafter provide methods and systems to improve EP map quality by a processor reducing the range of map values for the palette. The reduction is implemented by analyzing the EP values (e.g., LAT values) and classifying some of the data points as outlier data points. Excluding the values of these data points from the visible range (e.g., map scale) of EP values reduces the range of attribute values used to produce the map. In this way, regions which were previously difficult/impossible to distinguish are now well separated into regions of differing colors.

While outlier EP values may be hidden, hiding too many outliers may give a user a false feeling that there is no data captured in these areas. For this reason, other embodiments of the present invention show some of the EP value outliers—those that are considerably different from their neighbors, but by no more than a predefined "acceptable" value. Other outliers, whose EP values differ from their neighbors by more than the predefined acceptable value, are hidden.

In one embodiment, a processor receives a plurality of data points comprising EP values measured at respective positions in at least a portion of an organ of a patient, such as in a cardiac chamber. In alternative embodiment, the processor may also receive a modeled surface of at least a portion of a heart (e.g., an anatomical map) and the multiple EP values measured at multiple respective positions in the heart shown on the map.

Then, the processor classifies some of the EP values as outlier values in accordance with a defined criterion. The processor derives, from the plurality of data points, a visual representation of at least the portion of the organ that (i) represents the EP values with respective colors and (ii) visualizes less than all the outlier values, by performing one or both of (a) identifying outlier values that deviate from respective neighboring EP values by less than a defined deviation, and representing the identified outlier values using colors that match the neighboring EP values, and (b) setting for the visual representation a mapping, which maps the EP values to the colors and which excludes at least some of the outlier values. Finally, the processor displays the visual representation to a user.

In an optional embodiment, the processor interpolates over data points not classified as outliers, to derive a surface representation of the EP values over the mapped portion. The processor presents the surface representation of the EP values overlaid on the anatomical map, while graphically visualizing only outlier values falling within a predefined value by coloring only the outlier values according to a color code used in the interpolation.

In another embodiment, the processor graphically visualizes the surface representation of the EP values overlaid on the anatomical map using a scale that is narrowed by excluding the outlier values, so as to increase the map's color resolution.

In an embodiment, the number of outliers hidden depends on the relation between the EP value range and the color range. For example, when many colors are mapped to a small EP value range, the rest of the values receive the same color. Therefore, even if some points can be considered as outlier values according to some predefined threshold, in such a setting the processor may show them as conforming to the visual representation of the portion.

On the other hand, when colors are mapped to a wide range of EP values, small value difference between data points are reflected with different colors. Therefore, more data points will not be confirmed with the underlying map color. As such, more points will be considered as outliers and will be hidden.

Typically, the processor is programmed in software containing a particular algorithm that enables the processor to conduct each of the processor-related steps and functions outlined above.

By using the above-described graphical means, the disclosed techniques may assist the physician in the interpretation of EP maps and thus expedite and improve the quality of complicated diagnostic tasks, such as those required in diagnostic catheterizations.

System Description

FIG. 1 is a schematic, pictorial illustration of a system 21 for electrophysiological (EP) mapping, in accordance with an embodiment of the present invention. FIG. 1 depicts a physician 27 using a mapping Pentaray® catheter 29 to perform an EP mapping of a heart 23 of a patient 25. Catheter 29 comprises, at its distal end, one or more arms 20, which may be mechanically flexible, each of which is coupled with one or more electrodes 22. During the mapping procedure, electrodes 22 acquire and/or inject unipolar and/or bipolar signals from and/or to the tissue of heart 23. A processor 28 receives these signals via an electrical interface 35, and uses information contained in these signals to construct an EP map 31 stored by processor 28 in a memory 33. During and/or following the procedure, processor 28 may display EP map 31 on a display 26.

EP map 31 may be an LAT map, a bipolar potential map, or another map type. EP map 31 has an improved quality using the disclosed technique to derive and present confidence level on the map, as described in FIG. 2 and FIG. 3.

During the procedure, a tracking system is used to track the respective locations of sensing electrodes 22, such that each of the signals may be associated with the location at which the signal was acquired. For example, the Active Catheter Location (ACL) system, made by Biosense-Webster (Irvine, California), which is described in U.S. Pat. No. 8,456,182, whose disclosure is incorporated herein by reference, may be used. In the ACL system, a processor estimates the respective locations of the electrodes based on impedances measured between each of the sensing-electrodes 22, and a plurality of surface electrodes 24 that are coupled to the skin of patient 25. For example, three surface electrodes 24 may be coupled to the patient's chest and another three surface electrodes may be coupled to the patient's back. (For ease of illustration, only one surface electrode is shown in FIG. 1.) Electric currents are passed between electrodes 22 inside heart 23 of the patient and surface-electrodes 24. Processor 28 calculates an estimated location of all electrodes 22 within the patient's heart based on the ratios between the resulting current amplitudes measured at surface electrodes 24 (or between the impedances implied by these amplitudes) and the known positions of electrodes 24 on the patient's body. The processor may thus associate any given impedance signal received from electrodes 22 with the location at which the signal was acquired.

The example illustration shown in FIG. 1 is chosen purely for the sake of conceptual clarity. Other tracking methods can be used, such as ones based on measuring voltage signals. Other types of sensing catheters, such as the Lasso® Catheter (produced by Biosense Webster) or basket catheters may equivalently be employed. Physical contact sensors may be fitted at the distal end of mapping catheter 29 to estimate contact quality between each of the electrodes 22 and an inner surface of the cardiac chamber during measurement.

Processor 28 typically comprises a general-purpose computer with software programmed to carry out the functions described herein. In particular, processor 28 runs a dedicated algorithm as disclosed herein, including in FIG. 3, that enables processor 28 to perform the disclosed steps, as further described below. The software may be downloaded to the computer in electronic form, over a network, for example, or it may, alternatively or additionally, be provided and/or stored on non-transitory tangible media, such as magnetic, optical, or electronic memory.

Improved EP Map Coloration by Considering Outliers

Figure 2B:
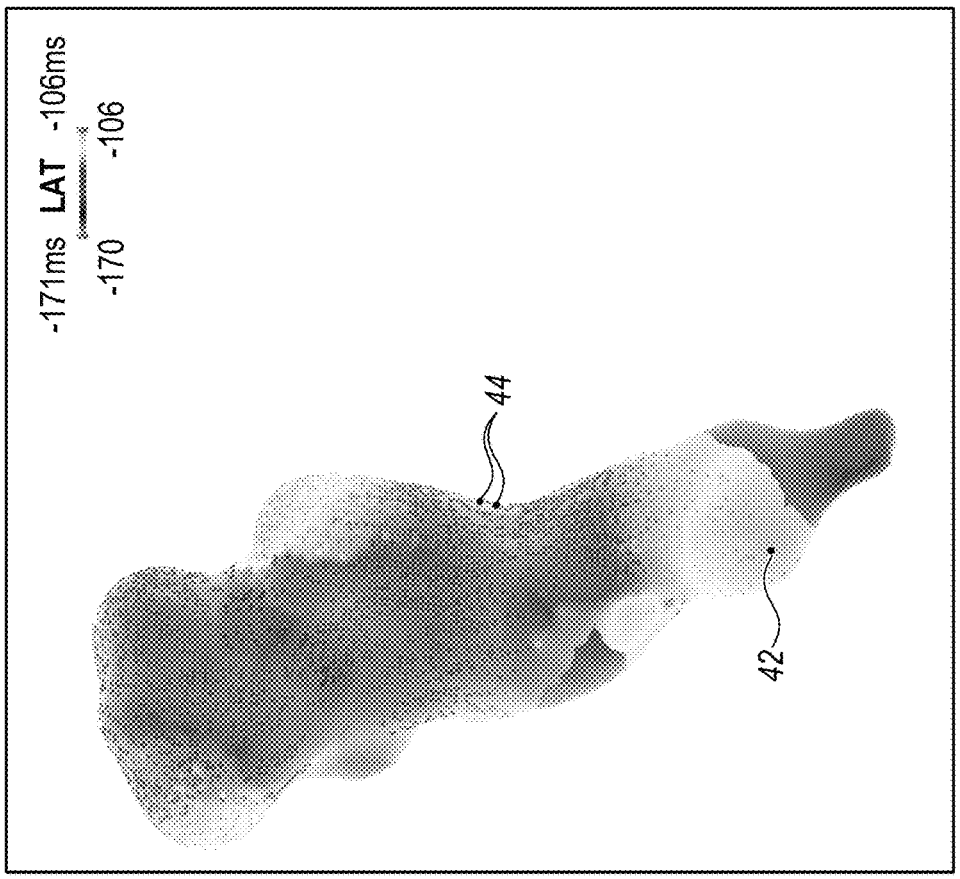
FIGS. 2A and 2B are schematic, pictorial volume renderings of, respectively, an EP map of a right atrium visualized with all outlier EP values, and the same EP map with only "allowable" outlier EP values visualized, in accordance with an exemplary embodiment of the present invention.
Figure 2A:
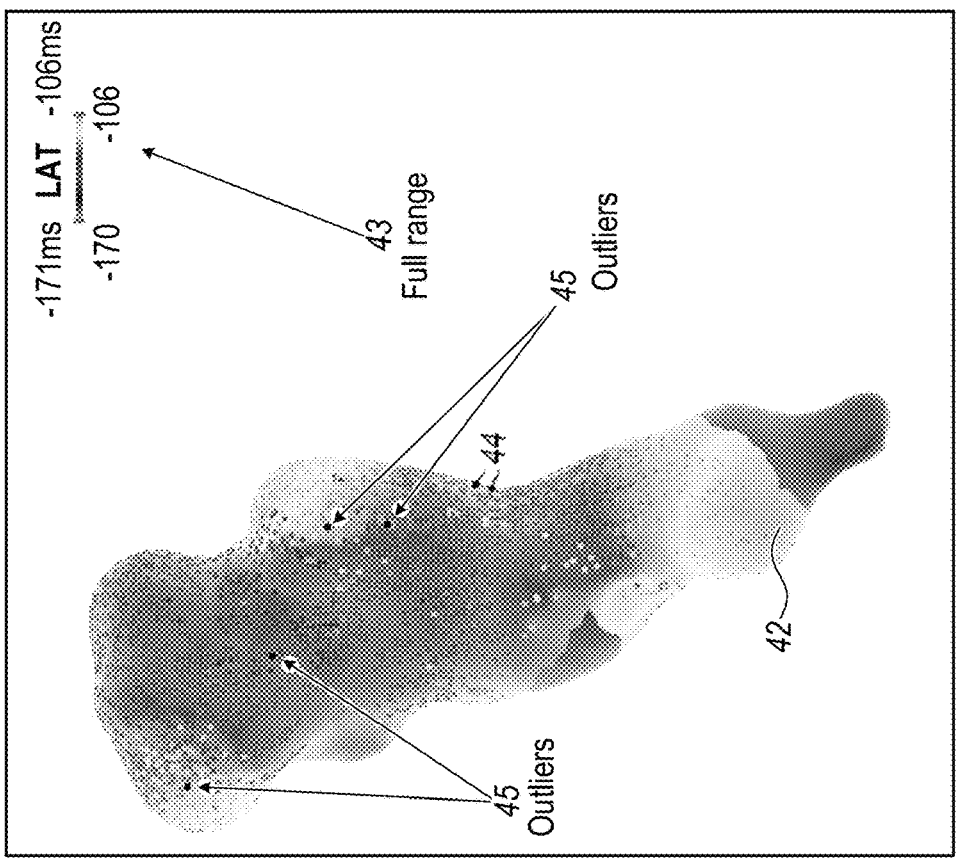

FIGS. 2A and 2B are schematic, pictorial volume renderings of, respectively, an EP map 42 of a right atrium visualized with all outlier EP values 45, and the same EP map with only a partial subset of "allowable" outlier EP values 44 visualized, in accordance with an embodiment of the present invention. As seen a same full color scale 43 is used with the two map presentations.

In the examples of FIGS. 2A and 2B (as well as in FIGS. 3A and 3B below), the EP values (e.g., LATs) of the data points are visualized using different grey levels drawn from a predefined greyscale. In real-life implementations the EP values are typically represented using colors drawn from some color palette, although greyscale implementations are also feasible. In the context of the present disclosure and in the claims, different grey levels are regarded as different colors, and references to colors and grey levels are used interchangeably.

While the outlier EP values 45 of FIG. 2A may be hidden, hiding too many outliers may give a user a false sense that no data was captured in these areas. As shown in FIGS. 2A and 2B, the disclosed techniques maintain some shown outliers (44), but only those that have an EP value relatively close, i.e., within a predefined value, to those of their neighbors. Other outliers are hidden. The resulting EP map is, at a same time, both sufficiently detailed and easier for a user interpret.

Figure 3B:
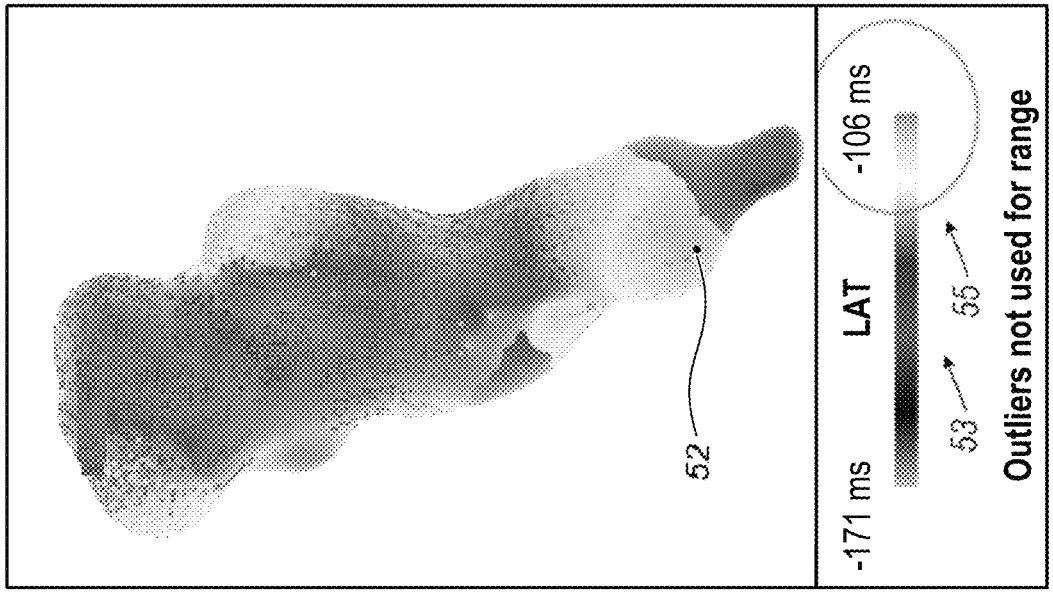
FIGS. 3A and 3B are schematic, pictorial volume renderings of, respectively, an EP map of a right atrium using a same color range for a full and narrowed attributed EP value ranges, in accordance with an exemplary embodiment of the present invention.
Figure 3A:
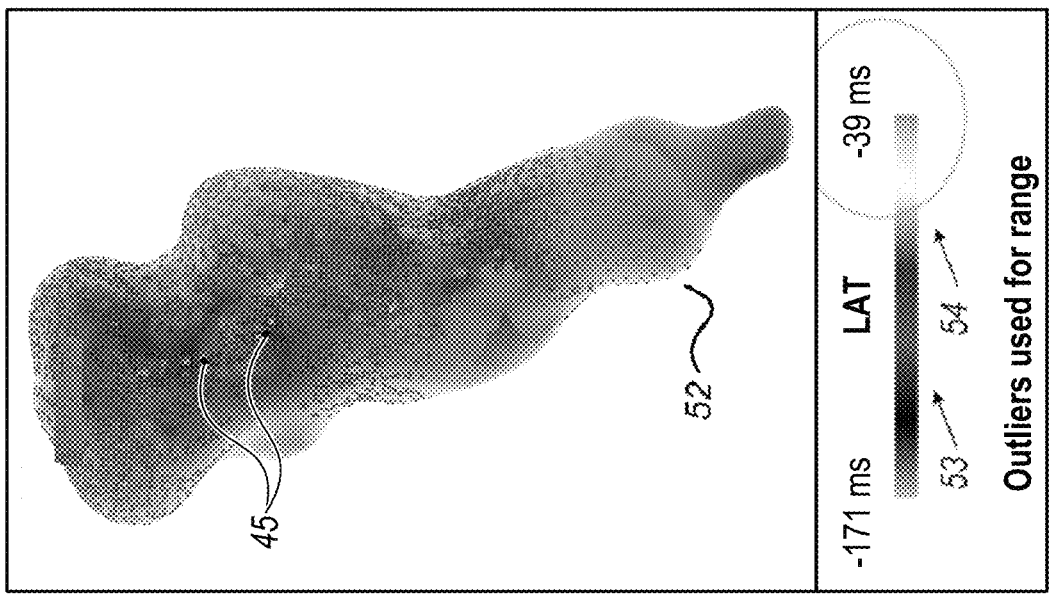

FIGS. 3A and 3B are schematic, pictorial volume renderings of, respectively, an EP map 52 of a right atrium using a same color range 53 for a full (54) and narrowed (55) attributed EP value ranges, in accordance with an embodiment of the present invention;

As seen in FIG. 3A, LAT map 52 is displayed with a wide range of LAT values (−171 ms to −39 ms). Most of the regions of the map are shades of similar colors (e.g., of yellow or green) and it is impossible to see small LAT value differences in these regions.

As seen in FIG. 3B, same LAT map 52 is displayed with a narrowed range of LAT values (−171 ms to −106 ms). The regions which were previously difficult/impossible to distinguish are now well separated into regions of different colors.

Figure 4:
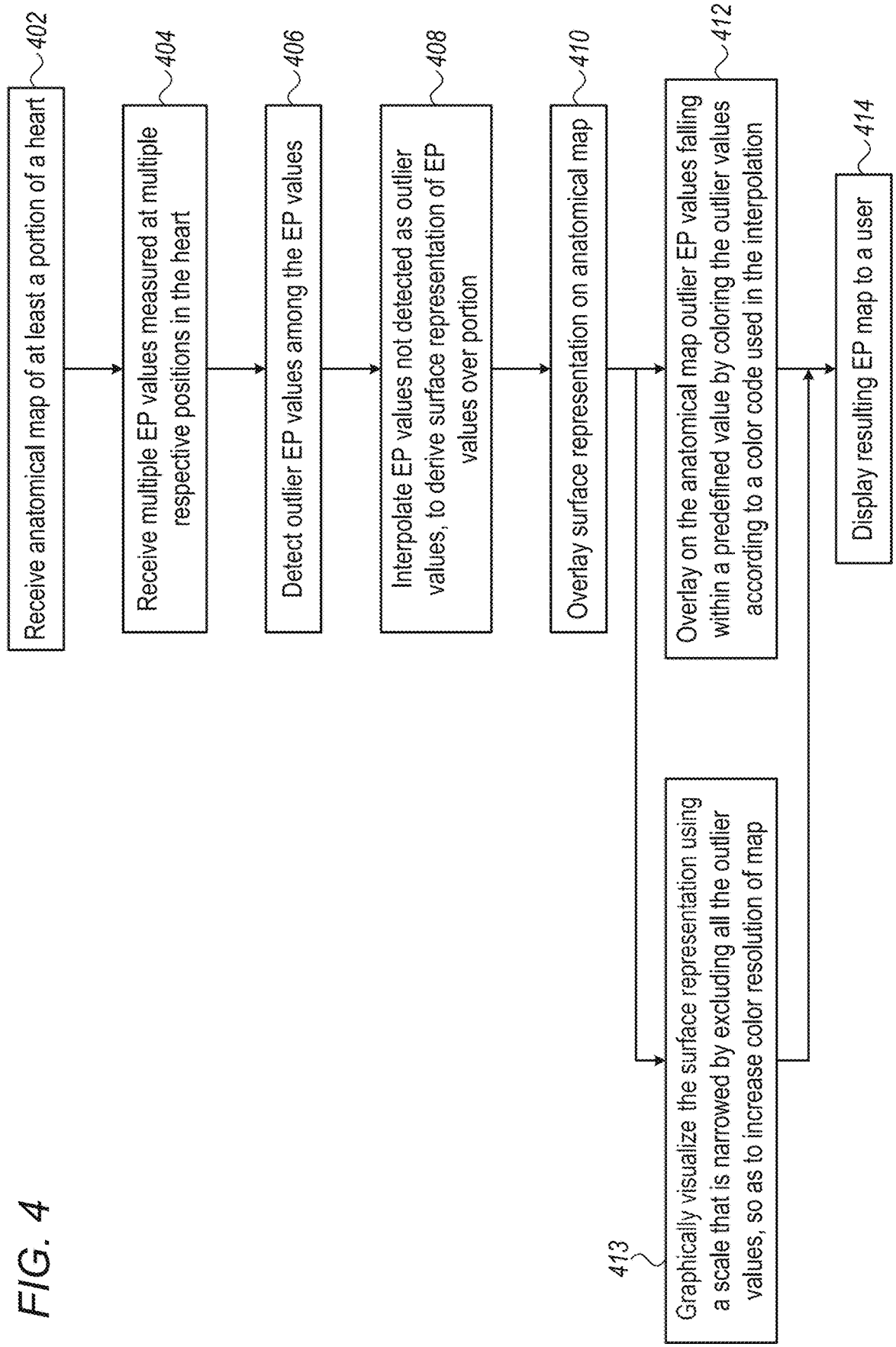
FIG. 4 is a flow chart that schematically illustrates a method for estimating and graphically visualizing EP values on the EP map of FIG. 2B and/or EP map FIG. 3B, in accordance with an exemplary embodiment of the present invention.

FIG. 4 is a flow chart that schematically illustrates a method for estimating and graphically visualizing EP values on the EP map of FIG. 2B and/or EP map FIG. 3B, in accordance with an embodiment of the present invention. The algorithm, according to the present embodiment, carries out a process that begins with processor 28 receiving a modeled surface (e.g., an anatomical map) of at least a portion of a heart, at a model receiving step 402.

At a data points receiving step 404, the processor revives multiple data points comprising EP values measured at multiple respective positions associated with the modeled surface. Step 404 may include all or part of the separate steps of acquiring electrograms using a multi-electrode catheter and processor 28 analyzing electrograms to derive EP values, such as LAT values.

Next, at outlier data points detection step 406, processor 28 detects, using a predefined criterion, the outlier EP values among the EP values received in step 404.

Next, at an interpolation step 408, processor 28 derives a surface representation of EP values not detected as outliers (typically the majority of EP values are correct) by interpolating the EP values. The output is a color scale map, such as surface representation 42.

Processor 28 then overlays the (color) surface representation on the anatomical map, at a surface representation overlying step 410.

Next, processor 28 may produce one or more EP maps by performing at least one of steps 412 and 413.

At an outlier displaying step 412, processor 28 overlays outlier EP values on the anatomical map that fall within a predefined value by coloring the outlier values, such as outlier 44, according to a color code used in the interpolation.

At a map graphical visualization step 413, processor 28 graphically visualizes the surface representation using a scale that is narrowed, as seen in FIG. 3B, by excluding all of the outlier values, so as to increase color resolution of the map.

Finally, at an EP map presentation step 414, processor 28 presents the one or more resulting EP maps to a user.

The example flow charts shown in FIG. 4 is chosen purely for the sake of conceptual clarity. In optional embodiments, various additional steps may be performed, for example to automatically register additional layers, such as of medical images, and to generate a display that can toggled among all layers.

Although the embodiments described herein mainly address cardiac applications, the methods and systems described herein can also be used in other applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
receiving, by a processor of a computing system, a plurality of data points comprising electrophysiological (EP) values measured at respective positions in at least a portion of the organ of the patient, wherein receiving the data points comprises acquiring the data points using a catheter;
classifying, by the processor of the computing system, some of the EP values as outlier values in accordance with a defined criterion;
deriving, by the processor of the computing system, from the plurality of data points, a visual surface color representation of at least the portion of the organ that (i) represents the EP values separated into regions with different respective colors and (ii) visualizes less than all the outlier values, by performing one or both of:
identifying, by the processor of the computing system, outlier values that deviate from respective neighboring EP values by less than a defined deviation, and representing each of these outlier values using colors that match the neighboring EP values; and
setting, by the processor of the computing system, for the visual representation a mapping, which maps the EP values to the colors and which excludes at least some of the outlier values;
causing, by the processor of the computing system, the visual surface color representation to be displayed to a user, the color resolution of the visual surface representation being increased by excluding the outlier values; and
performing diagnostic catheterization of the portion of the organ of the patient by the user using the increased resolution visual surface color representation of the organ having the EP values separated into regions of differing colors and the outlier values excluded.

2. The method according to claim 1, wherein deriving the visual representation comprises deriving an anatomical map.

3. The method according to claim 2, wherein deriving the anatomical map comprises generating the anatomical map by fast anatomical mapping (FAM).

4. The method according to claim 1, wherein the EP values are one of local activation times (LATs), bipolar potentials, or unipolar potentials.

5. The method according to claim 1, wherein deriving the visual representation comprises interpolating over the EP values not classified as outlier values.

6. The method according to claim 5, wherein representing the outlier values using colors that match the neighboring EP values comprises coloring the outlier values according to a color code used in interpolating the EP values.

7. A system, comprising:
an interface configured to receive a plurality of data points comprising electrophysiological (EP) values measured at respective positions in at least a portion of an organ of a patient, wherein the interface is configured to receive the data points from a catheter; and
a processor, which is configured to:
classify some of the EP values as outlier values in accordance with a defined criterion;
derive, from the plurality of data points, a visual surface color representation of at least the portion of the organ that (i) represents the EP values separated into regions with different respective colors and (ii) visualizes less than all the outlier values, by performing one or both of:
identifying outlier values that deviate from respective neighboring EP values by less than a defined deviation, and representing each of these outlier values using colors that match the neighboring EP values; and
setting for the visual representation a mapping, which maps the EP values to the colors and which excludes at least some of the outlier values;
cause the visual surface color representation to be displayed to a user, the color resolution of the visual surface representation being increased by excluding the outlier values; and
a catheter for performing diagnostic catheterization of the portion of the organ of the patient by the user using the increased resolution visual surface color representation of the organ having the EP values separated into regions of differing colors and the outlier values excluded.

8. The system according to claim 7, wherein the processor is configured to derive the visual representation by deriving an anatomical map.

9. The system according to claim 8, wherein the processor is configured to generate the anatomical map by fast anatomical mapping (FAM).

10. The system according to claim 7, wherein the EP values are one of local activation times (LATs), bipolar potentials, or unipolar potentials.

11. The system according to claim 7, wherein the processor is configured to derive the visual representation by interpolating over the EP values not classified as outlier values.

12. The system according to claim 11, wherein the processor is configured to represent the outlier values using colors that match the neighboring EP values by coloring the outlier values according to a color code used in interpolating the EP values.

* * * * *